(12) United States Patent
Kurihara et al.

(10) Patent No.: US 11,167,072 B2
(45) Date of Patent: Nov. 9, 2021

(54) SUCTION DISCHARGE UNIT AND SUCTION DISCHARGE DEVICE

(71) Applicant: Murata Manufacturing Co., Ltd., Kyoto (JP)

(72) Inventors: Kiyoshi Kurihara, Kyoto (JP); Susumu Takeuchi, Kyoto (JP); Kenichiro Kawamura, Kyoto (JP); Hiroaki Wada, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 263 days.

(21) Appl. No.: 16/420,309

(22) Filed: May 23, 2019

(65) Prior Publication Data

US 2019/0275218 A1 Sep. 12, 2019

Related U.S. Application Data

(63) Continuation of application No. PCT/JP2017/041993, filed on Nov. 22, 2017.

(30) Foreign Application Priority Data

Nov. 29, 2016 (JP) .............................. JP2016-231599
Mar. 21, 2017 (JP) .............................. JP2017-054809

(51) Int. Cl.
*A61M 1/00* (2006.01)

(52) U.S. Cl.
CPC ................. *A61M 1/74* (2021.05); *A61M 1/00* (2013.01); *A61M 1/0001* (2013.01);
(Continued)

(58) Field of Classification Search
CPC .............. A61M 1/0031; A61M 1/0001; A61M 2205/3341; A61M 2205/3348; A61M 1/0013; A61B 2217/005
See application file for complete search history.

(56) References Cited

U.S. PATENT DOCUMENTS 4,767,417 A * 8/1988 Boehringer ......... A61M 1/0013
604/31
4,963,135 A * 10/1990 Kerwin ............... A61M 1/0013
137/205
(Continued)

FOREIGN PATENT DOCUMENTS

EP    2022514 A2    2/2009
JP    H06-285156 A  10/1994
(Continued)

OTHER PUBLICATIONS

International Search Report for International Application No. PCT/JP2017/041993 dated Dec. 26, 2017.
(Continued)

*Primary Examiner* — Nicholas J Weiss
*Assistant Examiner* — Gregory J Feulner
(74) *Attorney, Agent, or Firm* — Peame & Gordon LLP

(57) ABSTRACT

A suction discharge unit of a suction discharge device includes a first unit and a second unit. The second unit controls the pressure inside the first unit. The first unit includes a storage chamber and a water sealing chamber. The water sealing chamber includes a first chamber communicating with the storage chamber, and a second chamber is sealed from the first chamber by sealing water. A negative pressure control unit is disposed in the second chamber. The negative pressure control unit includes a liquid retaining part retaining a liquid, a control member including control holes, and a support tube supporting the control member. The negative pressure control unit controls the pressure of the first chamber by causing gas to flow from the second chamber into the first chamber via the control holes and the liquid based on the pressure of the second chamber and the pressure of the first chamber.

17 Claims, 10 Drawing Sheets

(52) U.S. Cl.
CPC ............... *A61B 2217/005* (2013.01); *A61M 2205/3341* (2013.01); *A61M 2210/10* (2013.01)

(56) References Cited

U.S. PATENT DOCUMENTS

| | | | | |
|---|---|---|---|---|
| 4,994,050 | A * | 2/1991 | Weilbacher | A61M 1/0013 137/205 |
| 5,743,894 | A * | 4/1998 | Swisher | A61M 1/0013 604/319 |
| 10,143,781 | B1 * | 12/2018 | Pollen | A61M 1/0001 |
| 2018/0071440 | A1 * | 3/2018 | Takeuchi | A61M 1/0001 |

FOREIGN PATENT DOCUMENTS

| | | | |
|---|---|---|---|
| JP | H07-213599 | A | 8/1995 |
| JP | 2002-065843 | A | 3/2002 |

OTHER PUBLICATIONS

Written Opinion for International Application No. PCT/JP2017/041993 dated Dec. 26, 2017.

\* cited by examiner

SUCTION DISCHARGE UNIT AND SUCTION DISCHARGE DEVICE

This is a continuation of International Application No. PCT/JP2017/041993 filed on Nov. 22, 2017 which claims priority from Japanese Patent Application No. 2016-231599 filed on Nov. 29, 2016, and claims priority from Japanese Patent Application No. 2017-054809 filed on Mar. 21, 2017. The contents of these applications are incorporated herein by reference in their entireties.

BACKGROUND OF THE DISCLOSURE

Field of the Disclosure

The present disclosure relates to a suction discharge unit and a suction discharge device.

Description of the Related Art

In the related art, suction discharge devices that suck a bodily fluid or gas from a body cavity such as the chest of a subject after surgery by using the suction pressure of a continuously operating suction source are known (for example, refer to Patent Document 1). A liquid such as a sucked bodily fluid (hereafter, bodily fluid and the like) is stored in a transparent resin container (waste liquid container) called a suction bottle or a suction bag, and is then detached from the suction source at a suitable time and discarded. This type of waste liquid container is used such that a downstream space that is connected to the suction source and is subjected to negative pressure suction and an upstream space into which a bodily fluid and the like flows are isolated from each other, and such that the two spaces are water sealed from each other using sterile water.

Patent Document 1: Japanese Unexamined Patent Application Publication No. 7-213599

BRIEF SUMMARY OF THE DISCLOSURE

When the subject coughs or sneezes, the negative pressure inside the chest cavity or inside a container (storage chamber) of the suction discharge device connected to the inside of the chest cavity may become excessive. Such a negative pressure will damage the cellular tissues inside the body of the subject. Therefore, it is necessary for the nurse who is on duty to perform an operation to release the negative pressure of the container.

The present disclosure has been made in order to solve the above-described problem, and it is an object thereof to provide a suction discharge unit and a suction discharge device that are able to automatically prevent a negative pressure inside a storage chamber and a first chamber from becoming excessively large.

A suction discharge unit that solves the above-described problem is disposed between a subject and a suction source. The suction discharge unit includes: a first connection hole that communicates with the subject; a second connection hole that communicates with the suction source; a storage chamber that stores a first liquid that flows thereinto from the first connection hole; a water sealing chamber including a first chamber that communicates with the storage chamber and into which passage of the first liquid is prevented by a first partition wall and a second chamber that is isolated from the first chamber by a water sealing part and a second partition wall and that is connected to the suction source via the second connection hole; and a negative pressure control unit that controls a pressure of the first chamber by causing gas to flow from the second chamber to the first chamber on the basis of a pressure of the second chamber and the pressure of the first chamber. The negative pressure control unit includes a liquid retaining part that is able to retain a second liquid and is disposed such that the pressure of the second chamber acts on the second liquid, and a control member having a control hole for controlling inflow of the gas on the basis of surface tension of the second liquid.

According to this configuration, when the negative pressure of the storage chamber becomes excessive, the second liquid flows to the first chamber side of the control member via the control hole of the control member due to the pressure difference between the first chamber, which communicates with the storage chamber, and the second chamber. In addition to the pressure of the first chamber acting on the inflowing second liquid, the pressure of the second chamber also acts on the inflowing second liquid via the control hole. Therefore, gas in the second chamber flows to the first chamber side of the control member via the control hole, turns into bubbles and passes through the second liquid due to the pressure difference between the first chamber and the second chamber. That is, gas in the second chamber flows into the first chamber via the negative pressure control unit. The negative pressure of the first chamber, that is, the negative pressure of the storage chamber is reduced by this inflow of gas. Thus, it is possible to automatically prevent the negative pressure of the storage chamber and the first chamber from becoming excessively large. When the pressure difference between the first chamber and the second chamber reaches a prescribed value as a result of balance between the surface tension of the second liquid in the control hole, the pressure of the first chamber, and the pressure of the second chamber, a state is reached in which the inflow of gas to the first chamber stops and in which the second liquid is retained on the first chamber side of the control member. It is confirmed from the thus-retained second liquid that an excessive negative pressure is generated in the storage chamber.

In the above-described suction discharge unit, the negative pressure control unit includes a support tube that has a first end portion, the entire edge of the control member being attached to an inner periphery of the first end portion, and a second end portion that is open to the first chamber, the first end portion being disposed in the liquid retaining part. The negative pressure control unit stops the gas from flowing from the second chamber to the first chamber when the value of a sum of the pressure of the first chamber, a liquid pressure generated by the weight of the second liquid contained inside the support tube, and a surface tension of the second liquid is equal to the pressure of the second chamber.

According to this configuration, once the excessive negative pressure has been released, the pressure of the storage chamber, which communicates with the first chamber, can be controlled to a pressure corresponding to the liquid pressure generated by the weight of the second liquid and the pressure of the second chamber.

In the above-described suction discharge unit, the control hole has a circular shape, and the flow of the gas from the second chamber to the first chamber stops when $P1 + \rho g h + \sigma/R = P2$, where $P1$ is the pressure of the first chamber, $P2$ is the pressure of the second chamber, $\rho$ is the density of the second liquid, $g$ is the acceleration due to gravity, $h$ is the height of the second liquid retained in the support tube, $\sigma$ is a surface tension coefficient of the second liquid, and $R$ is the diameter of the control hole.

According to this configuration, once the excessive negative pressure has been released, the pressure of the storage chamber, which communicates with the first chamber, can be controlled to a pressure in accordance with the diameter of the control hole, and the density, height, and surface tension coefficient of the second liquid.

In the above-described suction discharge unit, the negative pressure control unit is accommodated in the second chamber.

According to this configuration, as a result of the negative pressure control unit being accommodated in the second chamber, since there is no need to connect a pipeline or the like to the outside in order to allow gas in the second chamber to flow from the second chamber to the first chamber via the negative pressure control unit, an increase in the size of the suction discharge unit can be suppressed.

The above-described suction discharge unit includes a control unit that communicates with the first chamber and the second chamber and that accommodates the negative pressure control unit. According to this configuration, a control unit in which the negative pressure control unit is accommodated is connected to the unit that includes the storage chamber and the water sealing chamber, and consequently, it is possible to reduce the negative pressure in the storage chamber and to easily confirm the generation of an excessive negative pressure.

The above-described suction discharge unit includes a filter between the storage chamber and the suction source. According to this configuration, bacteria can be prevented from entering a connection tube from the outside air by using a filter that does not allow the bacteria or the like to pass through the filter.

The above-described suction discharge unit includes a pressure adjusting chamber that has a second connection hole that communicates with the suction source, and the pressure adjusting chamber communicates with the second chamber via a connection pipe and adjusts the pressure of the second chamber.

According to this configuration, the pressure of the second chamber can be adjusted by the pressure adjusting chamber and the pressure of the first chamber and the storage chamber when suction is performed and the pressure of the first chamber and the storage chamber after an excessive pressure has been reduced can be set on the basis of the pressure of the second chamber.

The above-described suction discharge unit further includes: a liquid passage hole that is provided in the negative pressure control unit, that allows liquid retained on the first chamber side of the control member to flow into the liquid retaining part, and that has a larger opening area than the control hole; a valve body that can switch the liquid passage hole between a sealed state and an open state; and an urging member that is connected to the valve body and urges the valve body in a direction so as to seal the liquid passage hole.

According to this configuration, the liquid passage hole of a fixed member is put into an open state by the valve body, and as a result liquid retained in the support tube flows into the liquid retaining part via the liquid passage hole and the negative pressure control unit is reset to the initial state. In the case where an excessive negative pressure has been generated in the storage chamber again, liquid is retained in the support tube, and therefore it is possible to confirm from this retained liquid that an excessive negative pressure has been generated again in the storage chamber.

In the above-described suction discharge unit, the liquid passage hole is positioned at an identical height as the control hole or at a lower height than the control hole in a height direction.

According to this configuration, liquid retained above the control member flows into the liquid retaining part from the liquid passage hole and does not remain above the control member.

The above-described suction discharge unit further includes a seal releasing member that is connected to or contacts with the valve body and can be operated so as to release a sealed state of the liquid passage hole realized by the valve body.

According to this configuration, a sealed state of the liquid passage hole can be easily released by operating the valve body using the seal releasing member.

In the above-described suction discharge unit, the urging member has elasticity, and the seal releasing member releases the sealed state of the control hole realized by the valve body by causing the urging member to elastically deform.

According to this configuration, when operation of the seal releasing member is stopped, the valve body is urged in a direction so as to seal the liquid passage hole of the fixed member by the elastic force of the urging member and the liquid passage hole is thus easily put into a sealed state.

In the above-described suction discharge unit, the seal releasing member is a pressing member that presses the valve body and thereby releases the sealed state of the control hole realized by the valve body.

According to this configuration, the sealed state of the liquid passage hole of the fixed member can be easily released by operating the valve body using the seal releasing member, which is a pressing member.

In the above-described suction discharge unit, the seal releasing member is a separating member that separates the valve body from the control hole and thereby releases the sealed state of the control hole realized by the valve body.

According to this configuration, the sealed state of the liquid passage hole of the fixed member can be easily released by operating the valve body using the seal releasing member, which is a separating member.

A suction discharge device that solves the above-described problem includes: any one of the above-described suction discharge units; and a suction source that is connected to the suction discharge unit.

According to this configuration, it is possible to automatically prevent a negative pressure of the storage chamber and the first chamber from becoming excessively large by using the negative pressure control unit. In addition, it is confirmed from the state of the negative pressure control unit (state of second liquid) that an excessive negative pressure is generated in the storage chamber.

According to a suction discharge unit and a suction discharge device of the present disclosure, it is possible to automatically prevent a negative pressure of a storage chamber and a first chamber from becoming excessively large.

DETAILED DESCRIPTION OF THE DISCLOSURE

Hereafter, embodiments will be described. In the accompanying drawings, constitute elements may be illustrated in an enlarged manner to facilitate ease of understanding. Dimensional ratios of the constituent elements may differ from the actual ratios or may differ from the ratios in other drawings. Furthermore, in the sectional views, the hatching of some constituent elements may be omitted to facilitate ease of understanding.

First Embodiment

Figure 1:
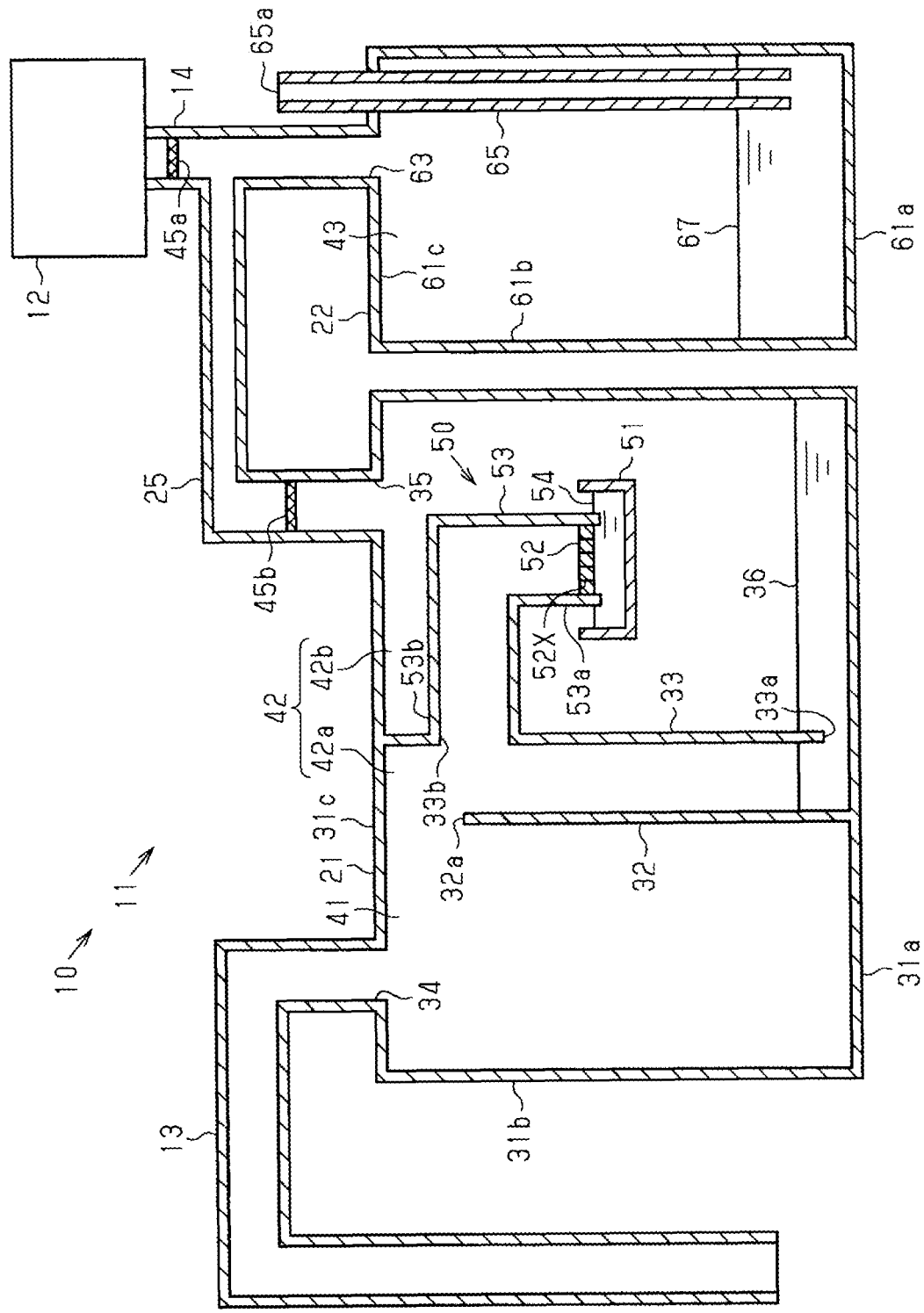
FIG. 1 is a schematic sectional view illustrating a suction discharge device of a first embodiment.

Hereafter, a first embodiment will be described. As illustrated in FIG. 1, a suction discharge device 10 includes a suction discharge unit 11 and a suction pump 12 functioning as a suction source.

The suction discharge unit 11 is connected to a subject via a connection tube 13. For example, the leading end of the connection tube 13 is inserted into the inside of the chest cavity of a patient who is the subject. Furthermore, the suction discharge unit 11 is connected to the suction pump 12 via the connection pipe 25. The suction pump 12 generates a negative pressure inside the suction discharge unit 11.

The suction discharge unit 11 includes a first unit 21 and a second unit 22. The first unit 21 and the second unit 22 are connected to each other by a connection pipe 25. In this embodiment, the suction pump 12 is connected to the connection pipe 25 via a connection pipe 14. Thus, the suction pump 12 is connected to the first unit 21 and the second unit 22.

The first unit 21 is, for example, formed in a box-like shape and includes a bottom plate part 31a, a side wall part 31b, and a top part 31c. In this embodiment, the side wall part 31b is formed in a cylindrical shape, and the bottom plate part 31a closes the lower end of the cylindrical side wall part 31b, and the top part 31c closes the upper end of the cylindrical side wall part 31b. A transparent material such as a transparent plastic is used as the material of the first unit 21 such that the inside of the first unit 21 can be observed from the outside.

The internal space of the first unit 21 is divided into a storage chamber 41 and a water sealing chamber 42 by a first partition wall 32. The first partition wall 32 is connected to the bottom plate part 31a and the side wall part 31b, and an upper end 32a of the first partition wall 32 is spaced apart from the top part 31c. Therefore, the storage chamber 41 and the water sealing chamber 42 communicate with each other in the upper part of the first unit 21, and a gas is able to move between the storage chamber 41 and the water sealing chamber 42.

In the storage chamber 41, a first connection hole 34 that allows the communication between the storage chamber 41 and the space outside the unit is formed in the top part 31c. The connection tube 13 is connected to the first connection hole 34. For example, the connection tube 13 is connected to a connection pipe (not illustrated) formed in the upper surface of the first unit 21. The first connection hole 34 allows the communication between the inside of the storage chamber 41 and the inside of the connection tube 13, in other words, the chest cavity of the subject.

The water sealing chamber 42 is divided into a first chamber 42a and a second chamber 42b by a second partition wall 33. The second partition wall 33 is connected to the top part 31c and the side wall part 31b, and a lower end 33a of the second partition wall 33 is spaced apart from the bottom plate part 31a. Therefore, the first chamber 42a and the second chamber 42b communicate with each other in a lower part of the first unit 21.

In other words, the internal space of the first unit 21 is divided into the storage chamber 41 and the water sealing chamber 42 by the first partition wall 32. The water sealing chamber 42 is divided into the first chamber 42a and the second chamber 42b by the second partition wall 33.

In the second chamber 42b, a second connection hole 35 that allows the communication between the second chamber 42b and the space outside the unit is formed in the top part 31c. The connection pipe 25 is connected to the second connection hole 35. For example, the connection pipe 25 is connected to a connection pipe (not illustrated) formed in the upper surface of the first unit 21. The second connection hole 35 allows the communication between the inside of the second chamber 42b and the inside of the connection pipe 25.

A filter 45a is disposed in the connection pipe 14. The filter 45a is a hydrophobic filter. The filter 45a allows a gas to pass therethrough and does not allow a liquid to pass therethrough. Therefore, the filter 45a prevents a liquid from entering the suction pump 12, which functions as a suction source.

A filter 45b is disposed in the connection pipe 25. The filter 45b is a bacteria filter that does not allow bacteria and the like to pass therethrough. The filter 45b is provided in order to prevent entry of bacteria into the connection tube 13 from the outside air. Therefore, it is sufficient that the filter 45b be provided closer to the outside air than the connection tube 13, and in this embodiment, the filter 45b is disposed in the connection pipe 25.

Sealing water 36, serving as a water sealing part, is accommodated in the water sealing chamber 42. The sealing water 36 is sterile water. In addition, the sealing water 36 may be colored. The sealing water 36 is stored in the water sealing chamber 42 such that the water surface in the first chamber 42*a* and the water surface in the second chamber 42*b* are higher than the lower end 33*a* of the second partition wall 33 in a state where the suction pump 12 is not operating.

The first unit 21 has a negative pressure control unit 50. In this embodiment, the negative pressure control unit 50 is accommodated in the second chamber 42*b* of the water sealing chamber 42.

The negative pressure control unit 50 includes a liquid retaining part 51, a control member 52, and a support tube 53.

The liquid retaining part 51 is disposed at a prescribed position using a support member, which is not illustrated. For example, the liquid retaining part 51 is fixed to the support tube 53, which will be described later, via the support member, which is not illustrated. In addition to being fixed to the support tube 53, the liquid retaining part 51 may be fixed in place using an inner wall of the second chamber 42*b* via a support member. The liquid retaining part 51 is formed so as to be able to retain a liquid 54. The liquid 54 is sterile water similarly to the sealing water 36 described above. The liquid 54 may be colored. The pressure inside the second chamber 42*b* acts on the liquid 54. The liquid 54 retained in the liquid retaining part 51 is supplied at the same time as the sealing water 36 in the water sealing chamber 42, for example. For example, the liquid 54 is supplied to the liquid retaining part 51. The liquid 54 that overflows from the liquid retaining part 51 is retained in the water sealing chamber 42 as the sealing water 36.

The control member 52 is formed to have a plate-like shape. The control member 52 includes control holes 52X that penetrate through the control member 52 in the thickness direction (up-down direction in figure). The control holes 52X are formed so as to have a prescribed shape. The control holes 52X are formed in a polygonal shape such as a triangular shape or one with a greater number of sides, or a circular shape or an elliptical shape, for example.

The control member 52 is suitably formed in order to control the surface tension of the liquid 54 described above. The thickness of the control member 52 may be 20 μm, for example. For example, in the case of a circular shape, the size of the control holes 52X can be 10-100 μm.

The control member 52 is fixed in place inside the support tube 53. The control member 52 is supported so as to contact with the liquid 54 retained in the liquid retaining part 51. For example, the control member 52 is fixed to a leading end 53*a* of the support tube 53, and the leading end 53*a* of the support tube 53 is disposed inside the liquid retaining part 51. More specifically, the leading end 53*a* of the support tube 53 is disposed inside the liquid 54 retained in the liquid retaining part 51.

A base end 53*b* of the support tube 53 is connected to the second partition wall 33. An opening 33*b* is formed in the second partition wall 33, and the inside of the first chamber 42*a* and the inside of the support tube 53 communicate with each other via the opening 33*b*. In other words, by using the support tube 53, the control member 52 is disposed between the first chamber 42*a* and the second chamber 42*b*, and the liquid 54 retained in the liquid retaining part 51 is disposed in the second chamber 42*b*.

The inner space of the second unit 22 functions as a pressure adjusting chamber 43 that adjusts the pressure (negative pressure) inside the first unit 21.

The second unit 22 is, for example, formed in a box-like shape and includes a bottom plate part 61*a*, a side wall part 61*b*, and a top part 61*c*. In this embodiment, the side wall part 61*b* is formed in a cylindrical shape, and the bottom plate part 61*a* closes the lower end of the cylindrical side wall part 61*b*, and the top part 61*c* closes the upper end of the cylindrical side wall part 61*b*. A transparent material such as a transparent plastic is used as the material of the second unit 22 such that the inside of the second unit 22 can be observed from the outside.

A third connection hole 63 that allows the communication between the inside of the second unit 22 and the outside is formed in the top part 61*c* of the second unit 22. The connection pipe 25 is connected to the third connection hole 63. For example, the connection pipe 25 is connected to a connection pipe (not illustrated) formed in the upper surface of the second unit 22. The third connection hole 63 allows the communication between the inside of the second unit 22 and the inside of the connection pipe 25. This connection pipe allows the communication between the inside of the second unit 22 and the water sealing chamber 42 (second chamber 42*b*) of the first unit 21.

The second unit 22 includes a thin pipe 65. In this embodiment, the upper end of the thin pipe 65 protrudes upward from the top part 61*c*, and the inside of the thin pipe 65 is open to the atmosphere via an opening 65*a* in the upper end of the thin pipe 65. The lower end of the thin pipe 65 is positioned in the vicinity of the bottom plate part 61*a*. The second unit 22 controls the pressure acting in the second chamber 42*b* of the water sealing chamber 42 via the depth of sterile water 67.

(Operation)

Next, operation of the above-described suction discharge device 10 will be described.

When the inside of the second unit 22 is made to have a negative pressure by the suction pump 12, the inside of the second unit 22 is maintained at a negative pressure corresponding to the height of the water surface of the sterile water 67. The inner space of the second unit 22 communicates with the inside of the first unit 21 and the second chamber 42*b* of the water sealing chamber 42 via the connection pipe 25. Therefore, the second unit 22 (pressure adjusting chamber 43) adjusts the pressure inside the first unit 21. For example, the second unit 22 (pressure adjusting chamber 43) adjusts the pressure of the second chamber 42*b* to a prescribed pressure (for example, −10 hPa from the atmospheric pressure).

In the first unit 21, the water level of the sealing water 36 in the second chamber 42*b* rises due to the negative pressure of the second chamber 42*b*, and the water level of the sealing water 36 in the first chamber 42*a* falls. Thus, the storage chamber 41 comes to have a prescribed negative pressure (for example, −8 hPa from the atmospheric pressure). The negative pressure of the storage chamber 41 is maintained by the suction pump 12 and the pressure adjusting chamber 43, and a suction force is applied to the chest cavity of the subject via the connection tube 13. Discharge liquid and gas such as air is guided from the chest cavity of the subject to the storage chamber 41 via the connection tube 13, and the discharge liquid is stored in the storage chamber 41. The gas passes under the lower end 33*a* of the second partition wall 33 from the first chamber 42*a* of the water sealing chamber 42, which communicates with the storage chamber 41, becomes air bubbles inside the sealing water 36, and reaches the second chamber 42*b*.

The negative pressure inside the storage chamber 41 may become excessive (for example, −40 hPa from the atmospheric pressure) as a result of the subject coughing or the like.

Figure 2:
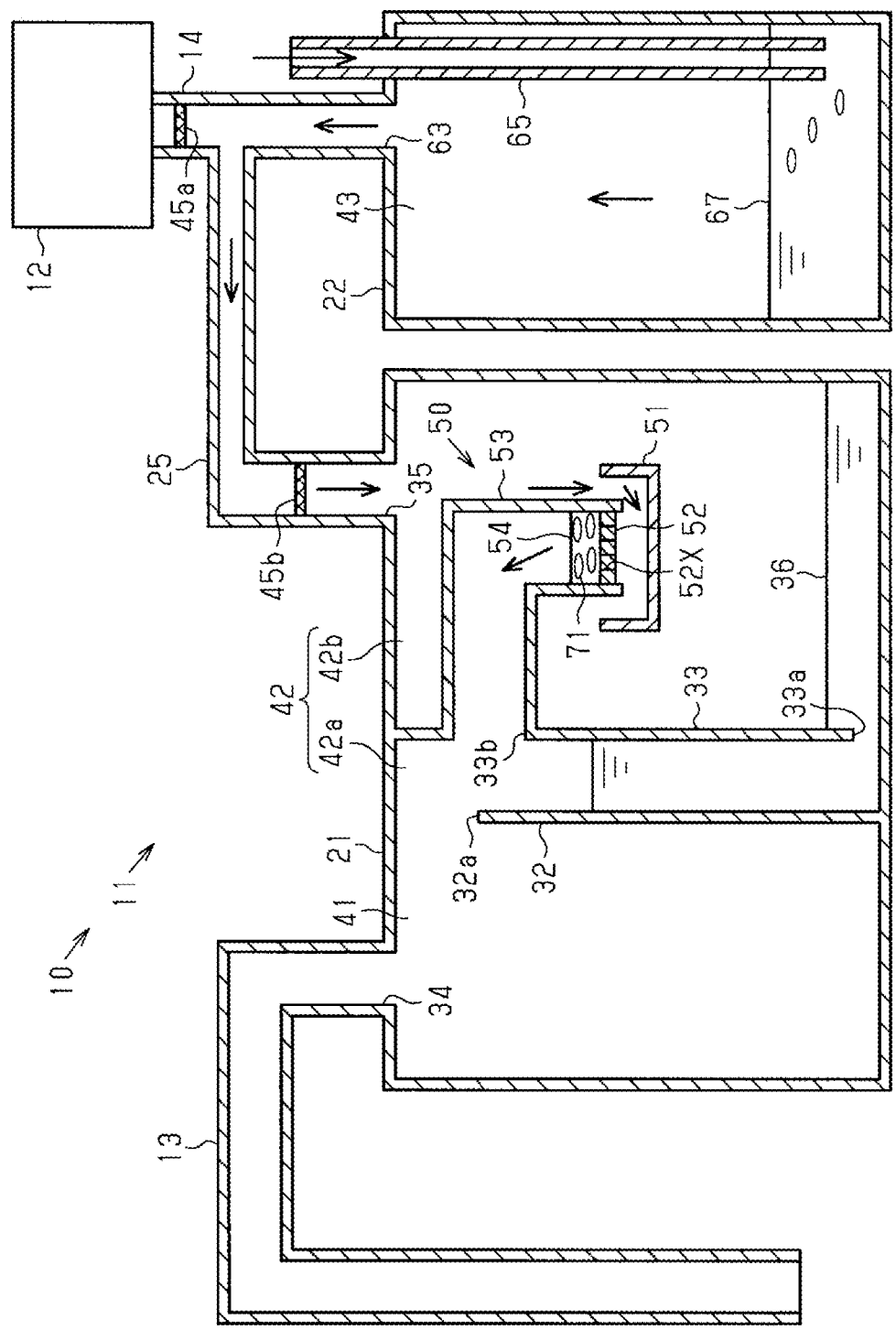
FIG. 2 is a schematic sectional view illustrating the operation of the suction discharge device of the first embodiment.

As illustrated in FIG. 2, the water level of the sealing water 36 in the first chamber 42*a* rises, and the water level in the second chamber 42b falls due to the negative pressure inside the storage chamber 41. At this time, the liquid 54 in the liquid retaining part 51 of the negative pressure control unit 50 flows into the support tube 53 via the control member 52 due to the pressure difference between the pressure of the storage chamber 41 (first chamber 42a) and the pressure of the second chamber 42b. In addition, gas inside the second chamber 42b flows into the inside of the support tube 53 via the control holes 52X of the control member 52, turns into the bubbles 71, and passes through the liquid 54. In other words, the negative pressure control unit 50 causes the gas inside the second chamber 42b to flow into the first chamber 42a (storage chamber 41) due to the pressure of the first chamber 42a (storage chamber 41) and the pressure of the second chamber 42b. Thus, the pressure inside the storage chamber 41 rises, and the excessive negative pressure is relieved by the gas being supplied to the storage chamber 41 from the second chamber 42b via the first chamber 42a.

Figure 3:
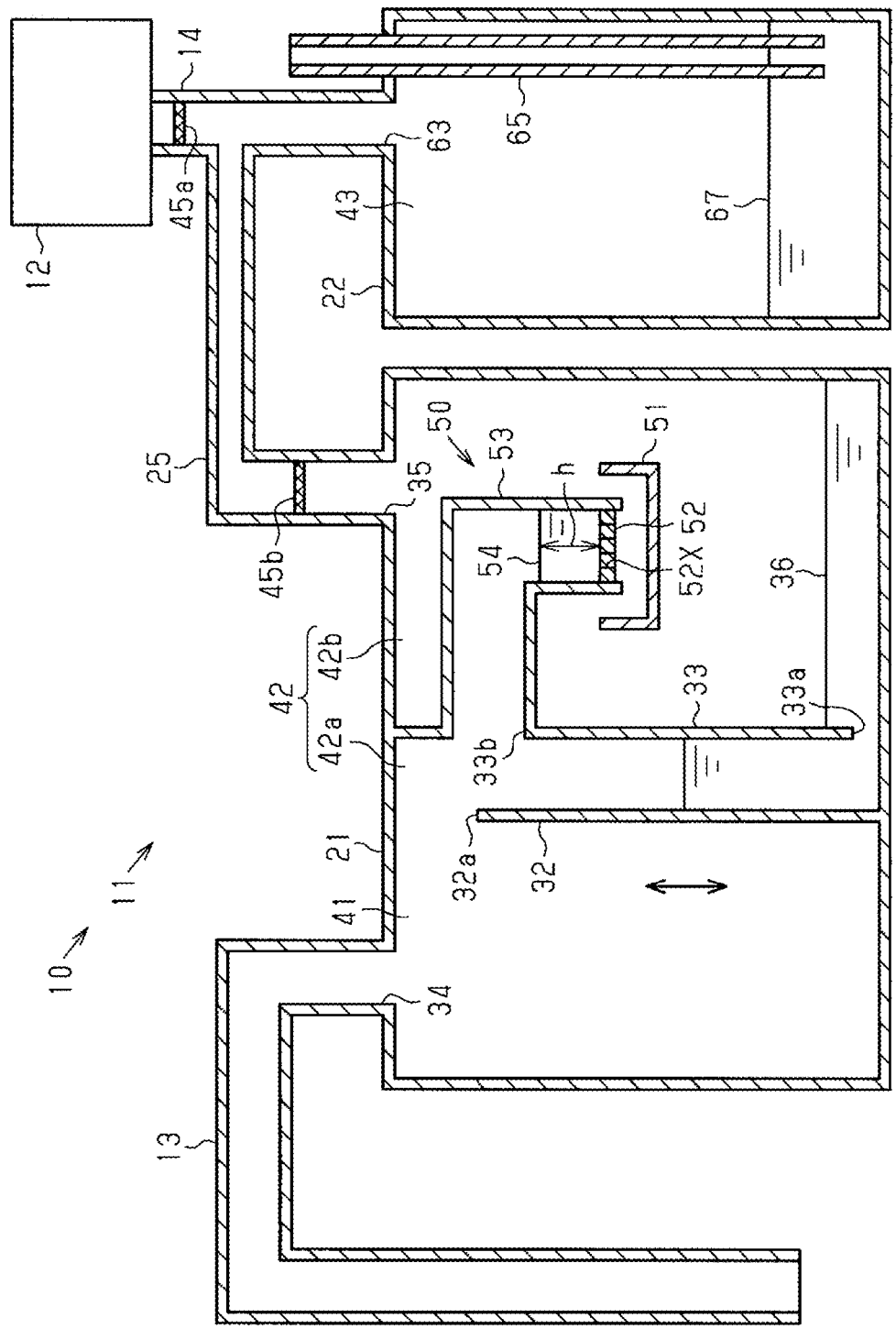
FIG. 3 is a schematic sectional view illustrating the operation of the suction discharge device of the first embodiment.

As illustrated in FIG. 3, when the pressure inside the storage chamber 41 falls from the excessive negative pressure, the water level of the sealing water 36 in the first chamber 42a, which communicates with the storage chamber 41, falls in accordance with this pressure. At this time, in addition to the pressure of the first chamber 42a acting on the liquid 54 inside the support tube 53 via the support tube 53, the pressure of the second chamber 42b also acts on the liquid 54 inside support tube 53 via the control holes 52X. When the pressure difference between the first chamber 42a and the second chamber 42b reaches a prescribed value as a result of balance being established between the surface tension of the liquid 54 at the control holes 52X, the pressure of the first chamber 42a, and the pressure of the second chamber 42b, a state is reached in which the gas stops flowing into the first chamber and in which the liquid 54 is retained inside the support tube 53. It is confirmed from the thus-retained liquid 54 that an excessive negative pressure is generated in the storage chamber 41.

Operation of the negative pressure control unit 50 will be described in detail.

Figure 4:
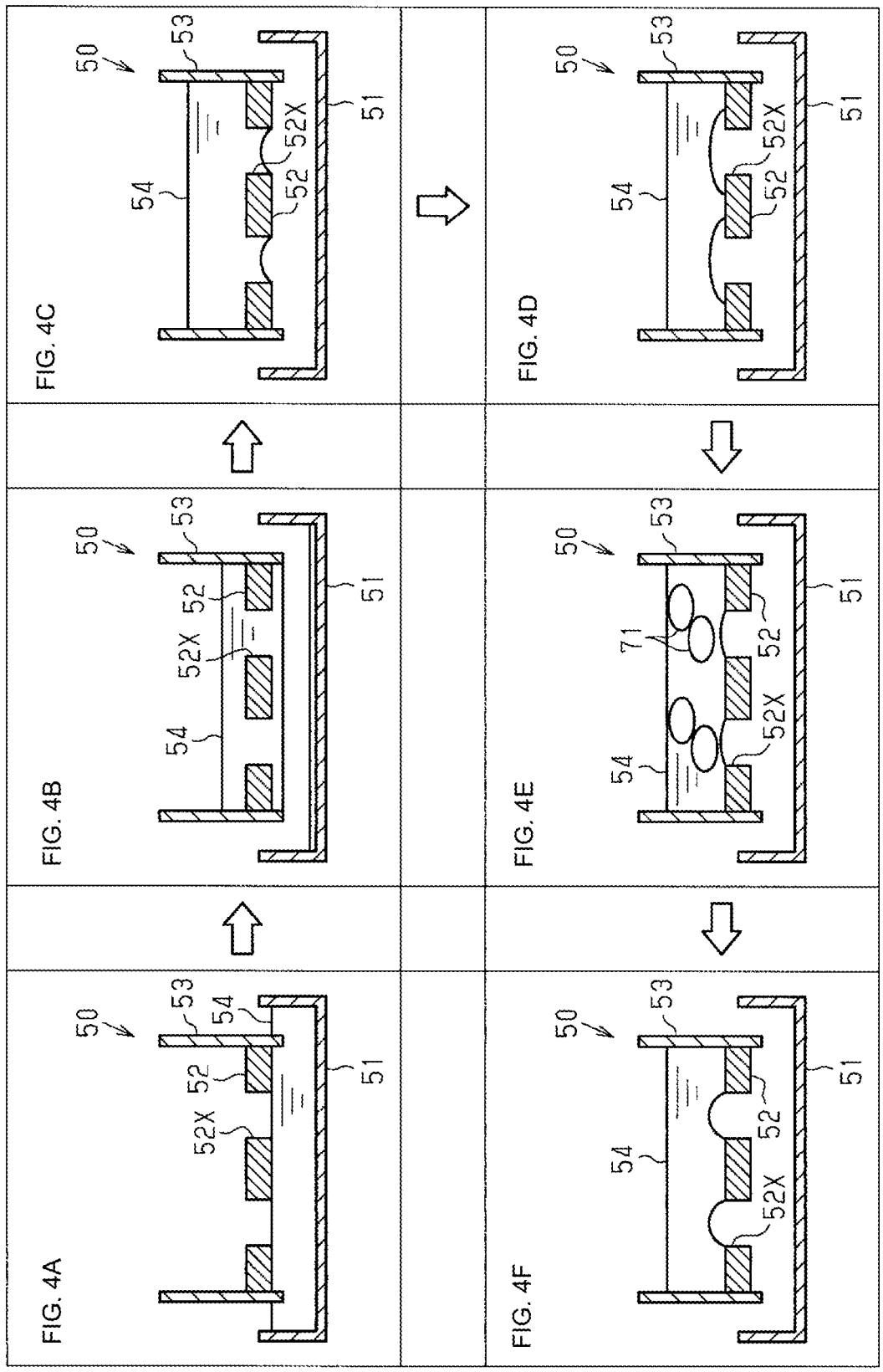
FIGS. 4A to 4F are schematic sectional views illustrating the operation of a negative pressure control unit of the first embodiment.

As illustrated in FIG. 4A, the liquid 54 is retained in the liquid retaining part 51 in an initial state (state where the negative pressure of storage chamber 41 is appropriate as illustrated in FIG. 1).

When the negative pressure of the storage chamber 41 becomes excessive as illustrated in FIG. 2, the liquid 54 in the liquid retaining part 51 flows into the inside of the support tube 53 via the control holes 52X of the control member 52 due to the negative pressure of the first chamber 42a, which communicates with the storage chamber 41, as illustrated in FIG. 4B. In addition, gas inside the second chamber 42b advances into the inside of the support tube 53 from the control holes 52X as illustrated in FIGS. 4C and 4D. Then, the gas turns into the bubbles 71 and passes through the liquid 54, as illustrated in FIG. 4E.

As illustrated in FIG. 3, when the value of the sum of the pressure of the first chamber 42a, the liquid pressure generated by the weight of the liquid 54 retained inside the support tube 53, and the surface tension at the surface of the liquid 54 generated by the control holes 52X is equal to the pressure of the second chamber 42b, the flow of gas from the second chamber 42b into the first chamber 42a stops. At this time, a state arises in which the liquid 54 is retained inside the support tube 53 due to the balance between the pressure of the storage chamber 41 and the first chamber 42a, the surface tension generated in the liquid 54 by the control holes 52X, and the pressure of the second chamber 42b.

The control holes 52X have a circular shape in this embodiment. R represents the diameter of the control holes 52X. $\rho$ represents the density of the liquid 54, $\sigma$ represents the surface tension coefficient of the liquid 54, h represents the height of the liquid 54 retained in the support tube 53, and g represents the acceleration due to gravity. When P1 represents the pressure of the first chamber 42a and P2 represents the pressure of the second chamber 42b, $P1 + \rho gh + \sigma/R = P2$ in the state illustrated in FIG. 4F. Therefore, the pressure of the storage chamber 41, which communicates with the first chamber 42a, can be controlled to a pressure according to the diameter R of the control holes 52X and the density $\rho$, height h, and surface tension coefficient $\sigma$ of the liquid 54.

As described above, according to this embodiment, the following effects are realized.

(1-1) The suction discharge device 10 includes the suction discharge unit 11 and the suction pump 12. The suction discharge unit 11 includes the first unit 21 and the second unit 22. The second unit 22 controls the pressure inside the first unit 21. The first unit 21 includes the storage chamber 41 and the water sealing chamber 42. The water sealing chamber 42 includes the first chamber 42a, which communicates with the storage chamber 41, and the second chamber 42b, which is sealed from the first chamber 42a by the sealing water 36.

The negative pressure control unit 50 is disposed in the second chamber 42b. The negative pressure control unit 50 includes the liquid retaining part that retains the liquid 54, the control member 52 that includes the control holes 52X, and the support tube 53 that supports the control member 52.

When the negative pressure of the storage chamber 41 becomes excessive, the liquid 54 flows into the inside of the support tube 53 via the control holes 52X of the control member 52 due to the pressure difference between the first chamber 42a, which communicates with the storage chamber 41, and the second chamber 42b. In addition to the pressure of the first chamber 42a acting on the liquid 54 inside the support tube 53 via the support tube 53, the pressure of the second chamber 42b also acts on the liquid 54 inside support tube 53 via the control holes 52X. Therefore, gas in the second chamber 42b flows into the inside of the support tube 53 via the control holes 52X, turns into the bubbles 71, and passes through the liquid 54 due to the pressure difference between the first chamber 42a and the second chamber 42b. That is, gas in the second chamber 42b flows into the first chamber 42a via the negative pressure control unit 50. The negative pressure of the first chamber 42a, that is, the negative pressure of the storage chamber 41 can be reduced by this inflow of gas. Thus, it is possible to automatically prevent the negative pressure of the storage chamber 41 and the first chamber 42a from becoming excessively large.

When the pressure difference between the first chamber 42a and the second chamber 42b reaches a prescribed value as a result of balance being established between the surface tension of the liquid 54 at the control holes 52X, the pressure of the first chamber 42a, and the pressure of the second chamber 42b, a state is reached in which the gas stops flowing into the first chamber 42a and in which the liquid 54 is retained inside the support tube 53. It can be confirmed from the thus-retained liquid 54 that an excessive negative pressure is generated in the storage chamber 41.

(1-2) The negative pressure control unit 50 stops the flow of gas from the second chamber 42b to the first chamber 42a when the value of the sum of the pressure of the first chamber 42a, the liquid pressure generated by the weight of the liquid 54 contained inside the support tube 53, and the surface tension of the liquid 54 becomes equal to the pressure of the second chamber 42b. Therefore, once the excessive negative pressure has been released, the pressure of the storage chamber 41, which communicates with the first chamber 42a, can be controlled to a pressure corresponding to the liquid pressure generated by the weight of the liquid 54 and the pressure of the second chamber 42b.

(1-3) In this embodiment, the negative pressure control unit 50 is disposed in the second chamber 42b. Therefore, since there is no need to connect a pipeline or the like to the outside in order to allow gas in the second chamber 42b to flow from the second chamber 42b to the first chamber 42a via the negative pressure control unit 50, an increase in the size of the suction discharge unit 11 can be suppressed.

(Modifications)

The first embodiment may be implemented in the following ways.

In the above-described embodiment, the negative pressure control unit 50 is disposed inside the water sealing chamber 42 (second chamber 42b) of the first unit 21, but the negative pressure control unit 50 may instead be disposed outside the first unit 21.

Figure 5:
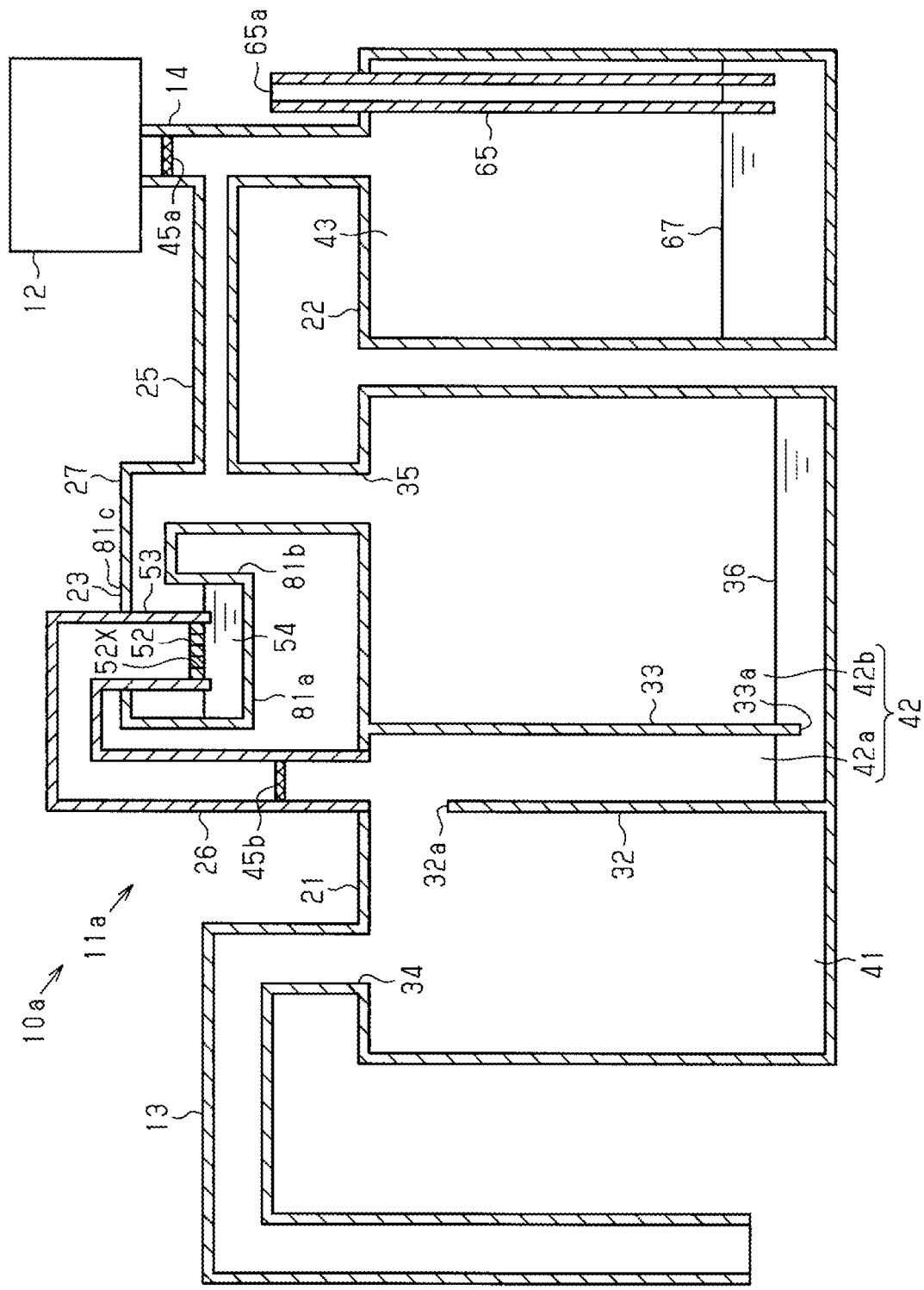
FIG. 5 is a schematic sectional view illustrating a modification of the suction discharge device of the first embodiment.

As illustrated in FIG. 5, a suction discharge unit 11a of a suction discharge device 10a includes the first unit 21, the second unit 22, and a third unit 23. The first unit 21 includes the storage chamber 41 and the water sealing chamber 42, and the water sealing chamber 42 includes the first chamber 42a and the second chamber 42b. The second unit 22 communicates with the first unit 21, and the second unit 22 is connected to the suction pump 12 and adjusts the pressure of the first unit 21.

The third unit 23 is, for example, formed in a box-like shape and includes a bottom plate part 81a, a side wall part 81b, and a top part 81c. A transparent material such as a transparent plastic is used as the material of the third unit 23 such that the inside of the third unit 23 can be observed from the outside.

The liquid 54 is retained in the third unit 23. A cap, which is not illustrated, is provided in a top part of the third unit 23, and the liquid 54 is retained inside the third unit 23 by opening and closing the cap. The support tube 53 is inserted into the inside of the third unit 23 from the top part 81c of the third unit 23, and the control member 52 is attached to the inside of the support tube 53. In other words, third unit 23 constitutes a negative pressure control unit.

The support tube 53 communicates with the first chamber 42a via a connection pipe 26 between the third unit 23 and the first unit 21. The inside of the third unit 23 communicates with the second chamber 42b via a connection pipe 27 and the connection pipe 25. The pressure of the second chamber 42b acts on the liquid 54 retained in the liquid retaining part 51 via the connection pipe 27 and the connection pipe 25. The filter 45b is disposed in the connection pipe 26 in the suction discharge unit 11a.

Similarly to the suction discharge device 10 of the above-described embodiment, the suction discharge device 10a can suppress an excessive negative pressure in the storage chamber 41 and the first chamber 42a. Furthermore, it can be confirmed from the state of the liquid 54 in the third unit 23 that an excessive negative pressure is generated.

In addition, an increase in the size of the suction discharge device 10a can be suppressed by the third unit 23. For example, it is thought that an excessive negative pressure in the storage chamber 41 and the first chamber 42a is suppressed by a unit having a thin pipe such as the second unit 22. However, the size of a unit having a thin pipe is increased in order to set the pressure, which results in an increase in the size of the suction discharge unit. In contrast, in the third unit 23 described above, the thickness of the control member 52, which functions as a valve for controlling gas flow, is for example 20 μm as described above. Therefore, the third unit 23 is smaller in size than a unit that uses a thin pipe. Therefore, an increase in size can be suppressed in the suction discharge device 10a in which the third unit 23 is connected to the outside of the first unit 21.

The shape of the negative pressure control unit 50 of the above-described embodiment may be changed as appropriate.

Figure 6:
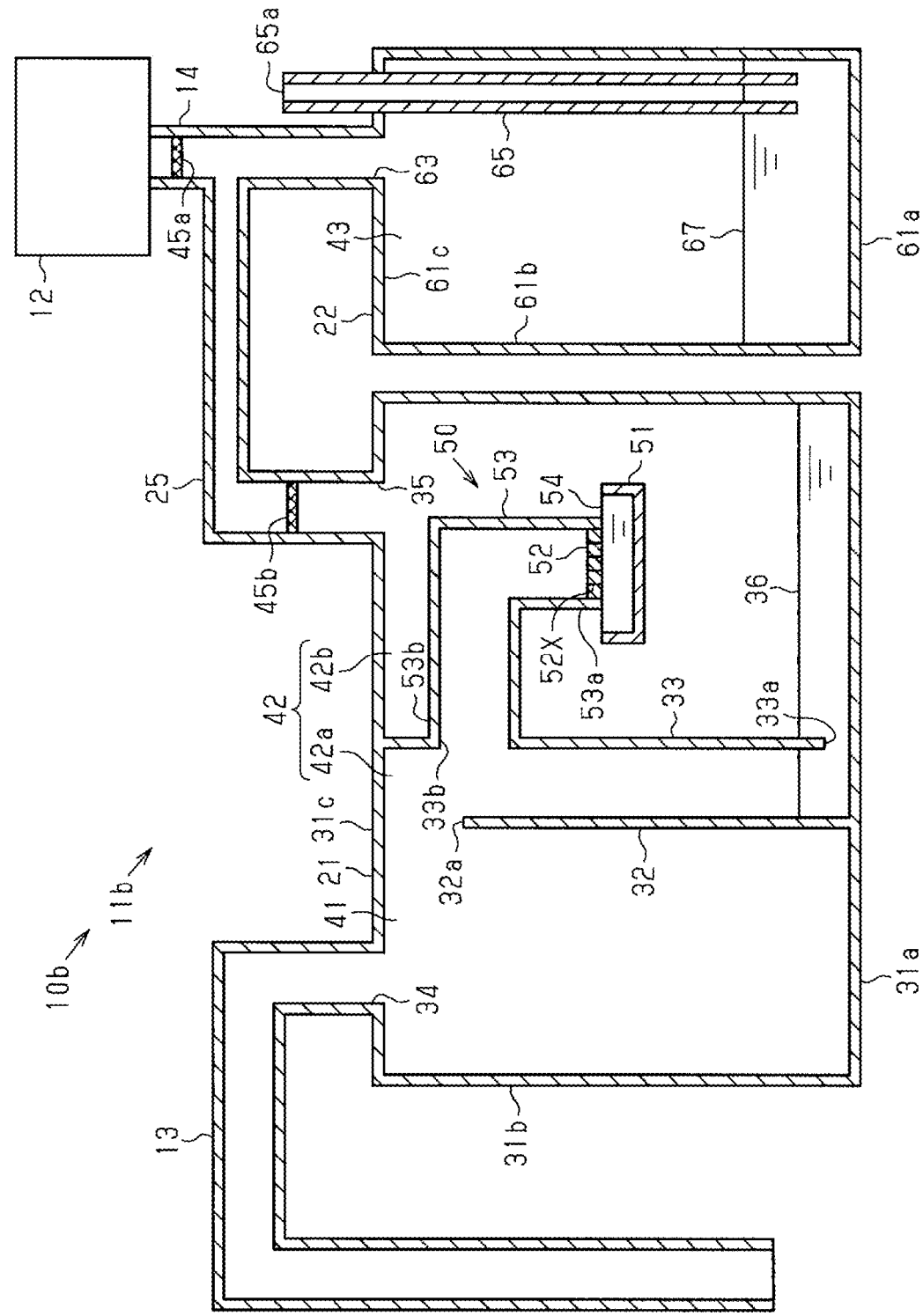
FIG. 6 is a schematic sectional view illustrating a modification of the suction discharge device of the first embodiment.

As illustrated in FIG. 6, the liquid 54 is retained in the liquid retaining part 51 of the negative pressure control unit 50 in a suction discharge unit 11b of a suction discharge device 10b. The control member 52 is attached to an end portion of the support tube 53 and is supported so as to contact with the liquid 54 retained in the liquid retaining part 51. The same operations and effects as in the above-described embodiment can also be obtained in the case where the control member 52 is supported in this way.

Second Embodiment

Hereafter, a second embodiment will be described.

In this embodiment, constituent members that are identical to those in the above-described embodiment will be denoted by identical symbols, and the description of such members will be partially or entirely omitted.

Figure 7:
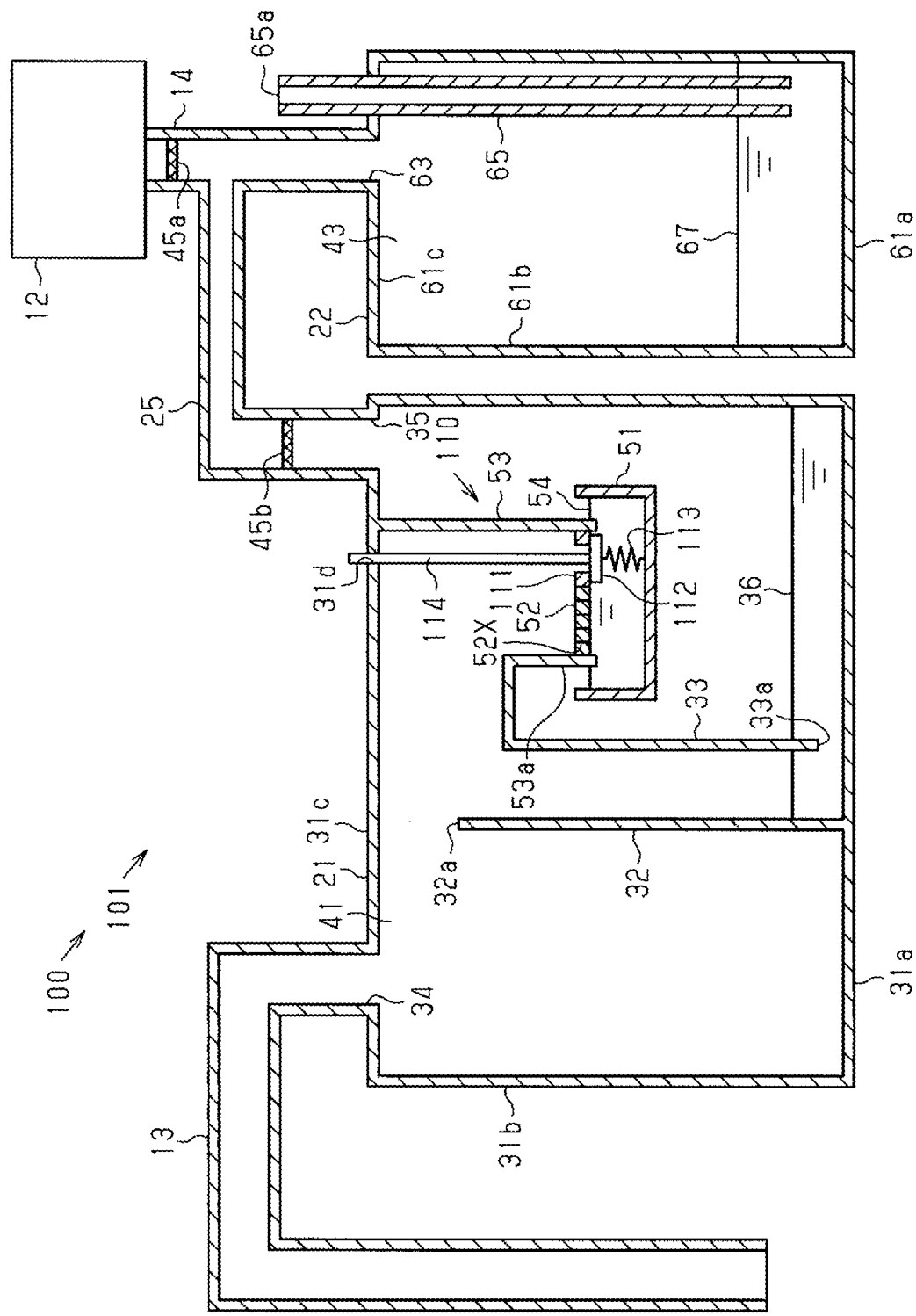
FIG. 7 is a schematic sectional view illustrating a suction discharge device of a second embodiment.

As illustrated in FIG. 7, a suction discharge device 100 includes a suction discharge unit 101 and the suction pump 12 functioning as a suction source.

The suction discharge unit 101 is connected to a subject via the connection tube 13. For example, the leading end of the connection tube 13 is inserted into the inside of the chest cavity of a patient who is the subject. Furthermore, the suction discharge unit 101 is connected to the suction pump 12 via the connection pipe 25. The suction pump 12 generates a negative pressure inside the suction discharge unit 101.

The suction discharge unit 101 includes the first unit 21 and the second unit 22.

The first unit 21 has a negative pressure control unit 110. In this embodiment, the negative pressure control unit 110 is accommodated in the second chamber 42b of the water sealing chamber 42.

The negative pressure control unit 110 includes the liquid retaining part 51, the control member 52, the support tube 53, a fixed member 111, a valve body 112, an urging member 113, and a seal releasing member 114.

The fixed member 111 is formed to have a plate-like shape. The fixed member 111 has a liquid passage hole 111X that penetrates through the fixed member 111 in the thickness direction (up-down direction in figure). The liquid passage hole 111X is formed in a prescribed shape.

In this embodiment, the fixed member 111 is disposed at a leading end 53a of the support tube 53. In addition, the fixed member 111 is disposed parallel to the control member 52. The fixed member 111 is disposed such that the liquid passage hole 111X of the fixed member 111 is at a prescribed position with respect to the control member 52. For example, the fixed member 111 is disposed such that the liquid passage hole 111X of the fixed member 111 is positioned at the same height as the control holes 52X of the control member 52 (upper edge of liquid passage hole 111X and upper edges of control holes 52X are at the same height).

In other words, the fixed member 111 is disposed such that the upper surface of the fixed member 111 and the upper surface of the control member 52 are positioned at the same height.

In addition, the fixed member 111 may be disposed such that the liquid passage hole 111X of the fixed member 111 is positioned at a lower height than the control holes 52X of the control member 52. In other words, the fixed member 111 may be disposed such that the upper surface of the fixed member 111 is positioned at a lower height than the upper surface of the control member 52.

The valve body 112 is disposed on the lower surface side of the fixed member 111. The valve body 112 is formed so as to be larger than the liquid passage hole 111X of the fixed member 111 and is formed so as to have a size so as to contact with the lower surface of the fixed member 111 along the entire periphery of the liquid passage hole 111X in a plan view. The valve body 112 seals the liquid passage hole 111X of the fixed member 111 in a state where the valve body 112 contacts with the lower surface of the fixed member 111. When the valve body 112 is separated from the fixed member 111, the liquid passage hole 111X of the fixed member 111 enters an open state. In other words, the valve body 112 makes the liquid passage hole 111X of the fixed member 111 switchable between a sealed state and an open state.

The urging member 113 is disposed between the lower surface of the valve body 112 and the liquid retaining part 51. The urging member 113 has elasticity and urges the valve body 112 in a direction so as to close the liquid passage hole 111X of the fixed member 111. For example, a compression spring can be used as the urging member 113.

The seal releasing member 114 is disposed above the valve body 112. The seal releasing member 114 is formed in a rod-like shape that extends in an up-down direction. In this embodiment, a lower end of the seal releasing member 114 is disposed on the upper surface of the valve body 112, and an upper end of the seal releasing member 114 protrudes to outside the first unit 21 from an insertion hole 31d formed in a top part 31c of the first unit 21. In this embodiment, the seal releasing member 114 is formed so as to be integrated with the valve body 112. When the seal releasing member 114 is pushed down against the urging force of the urging member 113, the valve body 112 is separated from the fixed member 111, and the liquid passage hole 111X of the fixed member 111 enters an open state.

(Operation)

Next, the operation of the above-described suction discharge device 100 will be described.

Similarly to the suction discharge device 10 of the first embodiment, the internal pressure of the second chamber 42b of the first unit 21 is adjusted to a prescribed pressure (for example, −10 hPa from atmospheric pressure) using the suction pump 12. Thus, the storage chamber 41 of the first unit 21 is made to be at a desired negative pressure (for example, −8 hPa from atmospheric pressure).

The negative pressure inside the storage chamber 41 may become excessive (for example, −40 hPa from the atmospheric pressure) as a result of the subject coughing or the like. In this case, the liquid 54 in the liquid retaining part 51 flows into the support tube 53 via the control member 52 due to the pressure difference between the pressure of the storage chamber 41 (first chamber 42a) and the pressure of the second chamber 42b. In addition, gas inside the second chamber 42b flows into the inside of the support tube 53 via the control holes 52X of the control member 52, turns into the bubbles 71, and passes through the liquid 54. In other words, the negative pressure control unit 110 causes the gas inside the second chamber 42b to flow into the first chamber 42a (storage chamber 41) due to the pressure of the first chamber 42a (storage chamber 41) and the pressure of the second chamber 42b. Thus, the pressure inside the storage chamber 41 rises, and the excessive negative pressure is relieved by the gas being supplied to the storage chamber 41 from the second chamber 42b via the first chamber 42a.

When the pressure inside the storage chamber 41 falls from the excessive negative pressure, the water level of the sealing water 36 in the first chamber 42a, which communicates with the storage chamber 41, falls in accordance with this pressure. When the pressure difference between the first chamber 42a and the second chamber 42b reaches a prescribed value as a result of balance being established between the surface tension of the liquid 54 at the control holes 52X, the pressure of the first chamber 42a, and the pressure of the second chamber 42b, a state is reached in which the gas stops flowing into the first chamber and in which the liquid 54 is retained inside the support tube 53. It is confirmed from the thus-retained liquid 54 that an excessive negative pressure is generated in the storage chamber 41.

Figure 8:
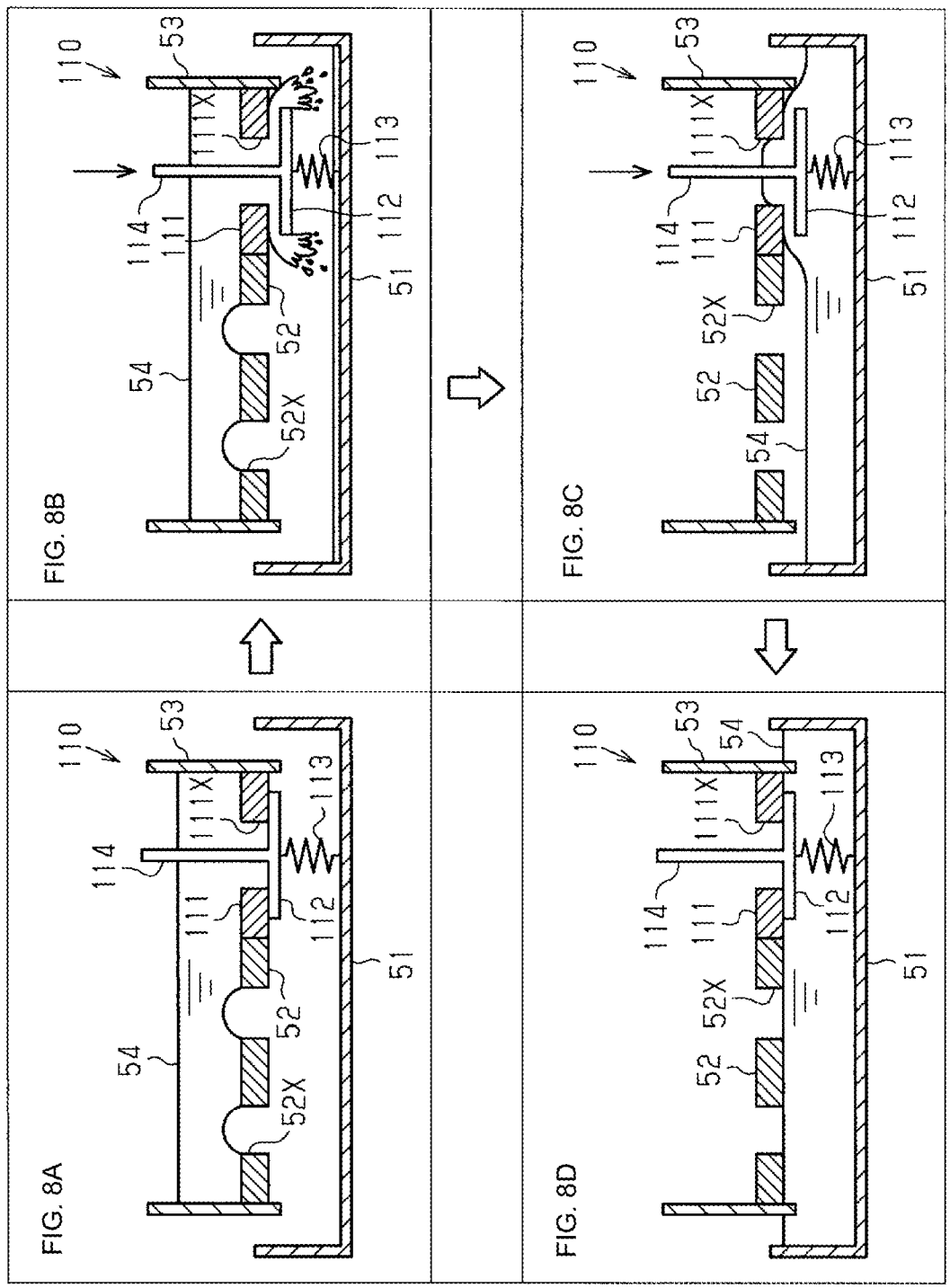
FIGS. 8A to 8D are schematic sectional views illustrating the operation of a negative pressure control unit of the second embodiment.

FIG. 8A illustrates a state in which the pressure inside the storage chamber 41 (refer to FIG. 7) has fallen from the excessive negative pressure due to the negative pressure control unit 110. The liquid 54 is retained on the upper side of the control member 52, that is, on the first chamber 42a side (storage chamber 41 side) of the control member 52. As illustrated in FIG. 8B, when a medical professional manually pushes the seal releasing member 114 down, the valve body 112 is pushed downward by the seal releasing member 114, and the liquid passage hole 111X of the fixed member 111 enters an open state. Thus, the retained liquid 54 flows into the liquid retaining part 51 via the liquid passage hole 111X.

Since the liquid passage hole 111X of the fixed member 111 is positioned at the same height as the control holes 52X of the control member 52, the liquid 54 disappears from the upper surface side of the control member 52, as illustrated in FIG. 8C. Then, as illustrated in FIG. 8D, when the medical professional releases his/her hand from the seal releasing member 114, the valve body 112 is made to closely contact with the lower surface of the fixed member 111 by the urging member 113. Thus, the liquid passage hole 111X of the fixed member 111 is put into a sealed state by the valve body 112.

In other words, the negative pressure control unit 110 is reset, i.e., returned to its initial state by the valve body 112, the fixed member 111, the urging member 113, and the seal releasing member 114.

Then, when an excessive negative pressure is once again generated in the storage chamber 41, the liquid 54 in the liquid retaining part 51 moves into the inside of the support tube 53 via the control holes 52X of the control member 52 and is retained inside the support tube 53. It can be confirmed from the thus-retained liquid 54 that an excessive negative pressure is generated. Then, once the confirmation has been made, the valve body 112 is pushed down by operating the seal releasing member 114 so as to put the liquid passage hole 111X of the fixed member 111 into an open state, the retained liquid 54 is allowed to flow out into the liquid retaining part 51, and the negative pressure control unit 110 is reset. Thus, by resetting the negative pressure control unit 110 after confirming the generation of an excessive negative pressure, it is possible to confirm the generation of an excessive negative pressure after this confirmation.

As described above, according to this embodiment, the following effects are realized in addition to the effects of the first embodiment.

(2-1) The negative pressure control unit 110 includes the liquid retaining part that retains the liquid 54, the control member 52 that includes the control holes 52X, and the support tube 53 that supports the control member 52. In addition, the negative pressure control unit 110 further includes the fixed member 111 including the liquid passage hole 111X, the valve body 112 that makes the liquid passage hole 111X of the fixed member 111 switchable between a sealed state and an open state, and an urging member 113 that urges the valve body 112 in a direction so as to seal the liquid passage hole 111X.

The liquid passage hole 111X of the fixed member 111 is put into an open state by the valve body 112, and as a result the liquid 54 retained in the support tube 53 flows into the liquid retaining part 51 via the liquid passage hole 111X, and the negative pressure control unit 110 is reset to the initial state. In the case where an excessive negative pressure is generated in the storage chamber 41 once again, the liquid 54 is retained in the support tube 53, and therefore it is possible to confirm that an excessive negative pressure has been generated once again in the storage chamber 41 from this retained liquid 54.

(2-2) The negative pressure control unit 110 includes the seal releasing member 114 that releases the sealing state of the liquid passage hole 111X of the fixed member 111 using the valve body 112, that is, puts the liquid passage hole 111X into an open state. When the liquid passage hole 111X is put into an open state, the liquid 54 retained inside the support tube 53, that is, retained on the first chamber 42a (storage chamber 41) side of the control member 52 is allowed to flow into the liquid retaining part 51, and thus, the negative pressure control unit 110 can be easily reset to the initial state.

(Modifications)

The second embodiment may be implemented in the following ways.

The various members included in the negative pressure control unit 110 of this embodiment may be changed as appropriate.

Figure 9:
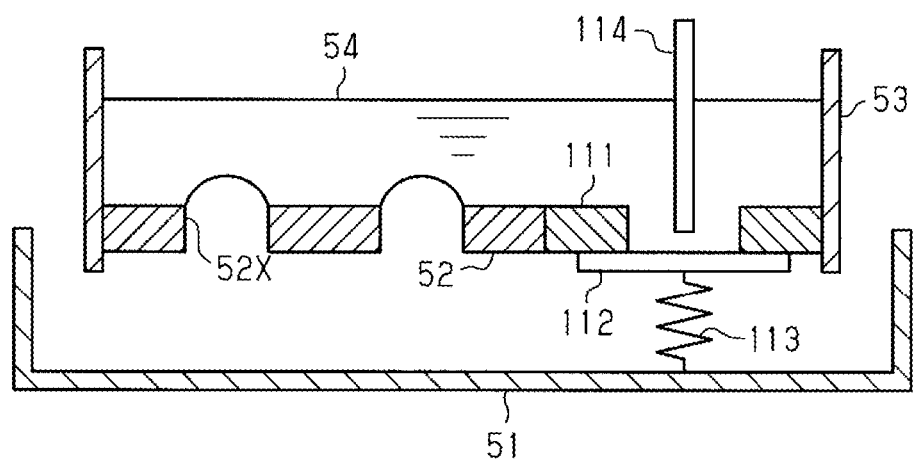
FIG. 9 is a schematic sectional view illustrating a modification of the negative pressure control unit of the second embodiment.

As illustrated in FIG. 9, the seal releasing member 114 and the valve body 112 may be provided as separate members.

Figure 10:
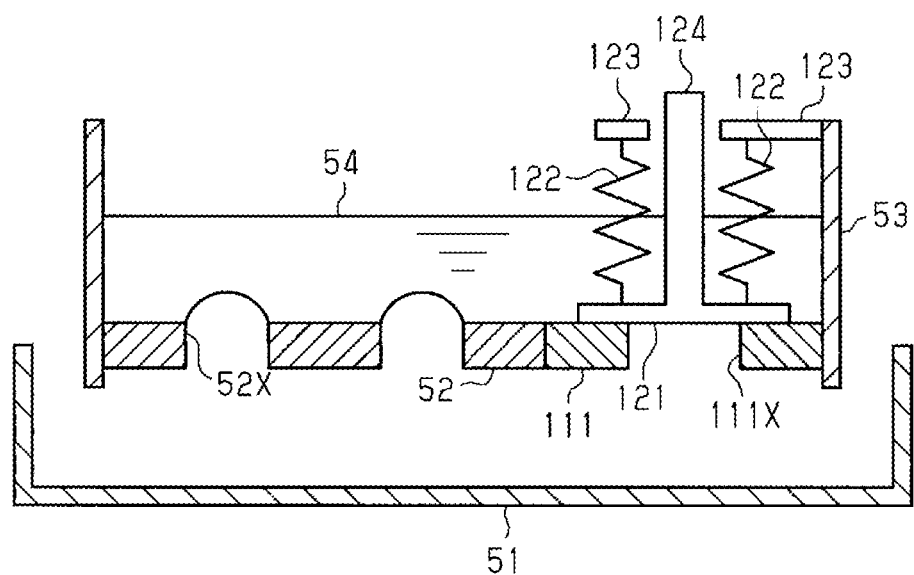
FIG. 10 is a schematic sectional view illustrating a modification of the negative pressure control unit of the second embodiment.

As illustrated in FIG. 10, a valve body 121 is disposed on the upper surface side of the fixed member 111. An urging member 122 is disposed above the fixed member 111 and between a support member 123, which is fixed to the support tube 53, and the valve body 121, and the urging member 122 urges the valve body 121 in a direction so as to seal the liquid passage hole 111X of the fixed member 111, i.e., toward the fixed member 111. For example, a compression spring can be used as the urging member 122. A seal releasing member 124 is fixed to the upper surface of the valve body 121. In FIG. 10, the valve body 121 and the seal releasing member 124 are illustrated as being integrated with each other. When the seal releasing member 124 is pulled upward and the valve body 121 is separated from the fixed member 111, the liquid 54 retained on the first chamber 42a side of the control member 52 (refer to FIG. 7) flows into the liquid retaining part 51 from the liquid passage hole 111X of the fixed member 111. In this case, the seal releasing member 124 functions as a separating member that separates the valve body 121 from the fixed member 111.

In addition, the seal releasing member 124 and the valve body 121 may be provided as separate members. The seal releasing member 124 and the valve body 121 may be provided so as to be integrated with each other by integrating the lower end of the seal releasing member 124 with an insertion hole formed in the valve body 121 using press fitting, an adhesive, or the like. Furthermore, the seal releasing member 124 and the valve body 121 may be integrated with each other by forming a male screw thread on the lower end of the seal releasing member and forming a female screw thread in an insertion hole in the valve body 121 and then screwing these threads together.

Figure 11:
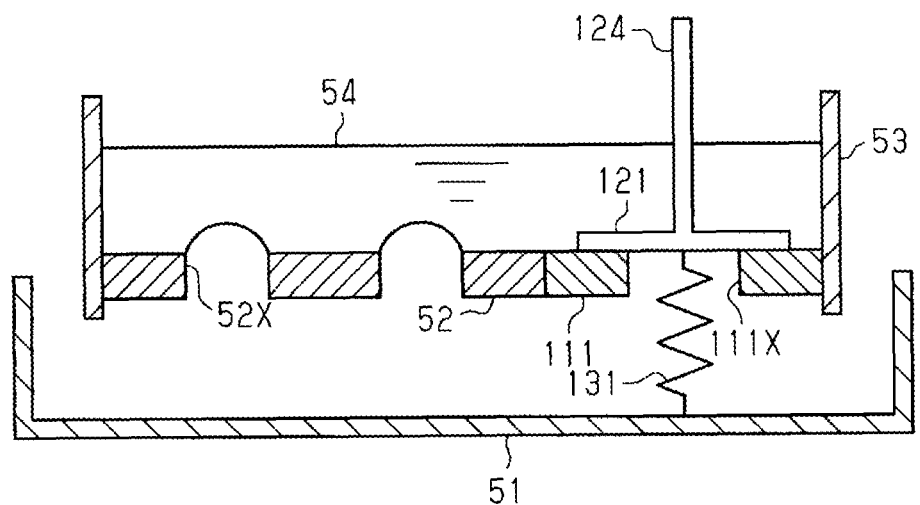
FIG. 11 is a schematic sectional view illustrating a modification of the negative pressure control unit of the second embodiment.

As illustrated in FIG. 11, the valve body 121 is disposed on the upper surface side of the fixed member 111. An urging member 131 is disposed between the lower surface of the valve body 121 and the liquid retaining part 51 and urges the valve body 121 in a direction so as to seal the liquid passage hole 111X of the fixed member 111, that is, toward the upper surface of the fixed member 111. For example, a pull spring can be used as the urging member 131. A seal releasing member 124 is fixed to the upper surface of the valve body 121. In FIG. 11, the valve body 121 and the seal releasing member 124 are illustrated as being integrated with each other. When the seal releasing member 124 is pulled upward and the valve body 121 is separated from the fixed member 111, the liquid 54 retained on the first chamber 42a side of the control member 52 (refer to FIG. 7) flows into the liquid retaining part 51 from the liquid passage hole 111X of the fixed member 111. In this case, the seal releasing member 124 functions as a separating member that separates the valve body 121 from the fixed member 111.

Figure 12:
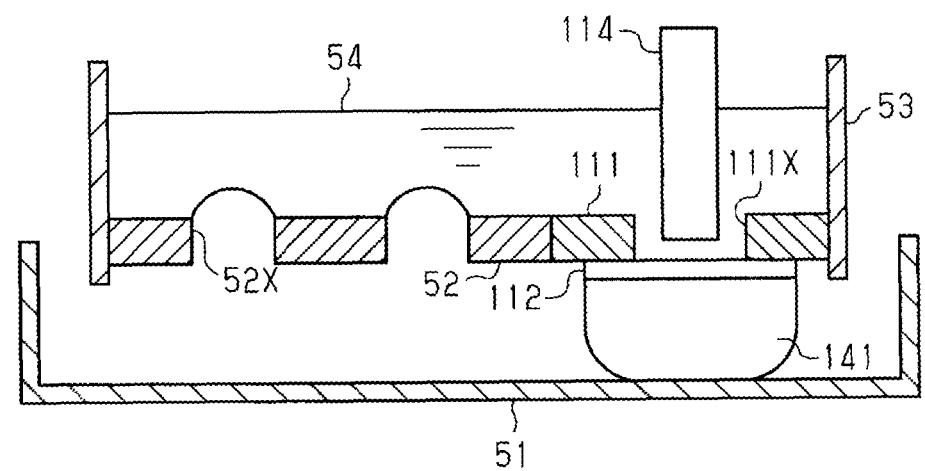
FIG. 12 is a schematic sectional view illustrating a modification of the negative pressure control unit of the second embodiment.

As illustrated in FIG. 12, the valve body 112 is disposed on the lower surface side of the fixed member 111. An urging member 141 is disposed between the lower surface of the valve body 112 and the liquid retaining part 51, and the urging member 141 urges the valve body 112 in a direction so as to seal the liquid passage hole 111X of the fixed member 111, that is, toward the upper surface of the fixed member 111. A material having elasticity such as rubber can be used for the urging member 141 and the urging member 141 is fixed to the lower surface of the valve body 112. A hollow member such as a balloon can also be used as the urging member. The valve body 112 and the seal releasing member 114 are illustrated as being separate members in FIG. 12, but the valve body 112 and the seal releasing member 114 may instead be integrated with each other.

(Modifications)

The above embodiments may be implemented in the following ways.

In the above-described embodiments, the suction discharge unit 11 that includes the first unit 21 and the second unit 22 is described, but a suction discharge unit in which the first unit 21 and the second unit 22 are integrated with each other may instead be adopted.

In the above-described embodiments, a pump that allows pressure setting may be used as the suction pump 12 and the second unit 22 may be omitted.

In the above-described embodiments, the storage chamber 41 and the water sealing chamber 42 may be formed as separate containers (units) and may be connected to each other such that the first chamber 42a of the water sealing chamber 42 and the storage chamber 41 communicate with each other. Furthermore, the first chamber 42a and the second chamber 42b of the water sealing chamber 42 may be formed as separate containers and may be connected to each other so as to be isolated from each other by the sealing water 36 functioning as a water sealing part.

10 . . . suction discharge device,
11 . . . suction discharge unit,
12 . . . suction pump (suction source),
34 . . . first connection hole,
35 . . . second connection hole,
32 . . . first partition wall,
33 . . . second partition wall,
41 . . . storage chamber,
42 . . . water sealing chamber,
42a . . . first chamber,
42b . . . second chamber,
43 . . . sealing water (water sealing part),
50 . . . negative pressure control unit,
51 . . . liquid retaining part,
52 . . . control member,
52X . . . control hole,
53 . . . support tube,
54 . . . liquid,
100 . . . suction discharge device,
101 . . . suction discharge unit,
110 . . . negative pressure control unit,
111 . . . fixed member,
111X . . . liquid passage hole,
112 . . . valve body,
113 . . . urging member,
114 . . . seal releasing member.

The invention claimed is:

1. A suction discharge unit disposed between a subject and a suction source, comprising:
a first connection hole communicating with the subject;
a second connection hole communicating with the suction source;
a storage chamber storing a first liquid flowing into the storage chamber from the first connection hole;
a water sealing chamber including a first chamber, a second chamber, a first partition wall, a second chamber, a water sealing part and a second partition wall, wherein the first chamber communicates with the storage chamber, the first partition wall prevents the first liquid from passing into the first chamber, and the second chamber is isolated from the first chamber by the water sealing part and the second partition wall and is connected to the suction source via the second connection hole; and
a negative pressure control unit controlling a pressure of the first chamber by causing a gas to flow from the second chamber to the first chamber based on a pressure of the second chamber and the pressure of the first chamber;
wherein the negative pressure control unit includes a liquid retaining part allowing a second liquid to be retained and disposed such that the pressure of the second chamber acts on the second liquid, and
a control hole for controlling an inflow of the gas based on a surface tension of the second liquid.

2. The suction discharge unit according to claim 1, further comprising a control member having the control hole,
wherein the negative pressure control unit includes a support tube having a first end portion and a second end portion, wherein an entire edge of the control member is attached to an inner periphery of the first end portion, the second end portion is open to the first chamber, and the first end portion is disposed in the liquid retaining part, and the negative pressure control unit stops the gas from flowing from the second chamber to the first chamber when a value of a sum of the pressure of the first chamber, a liquid pressure generated by a weight of the second liquid contained inside the support tube, and a surface tension of the second liquid is equal to the pressure of the second chamber.

3. The suction discharge unit according to claim 2, wherein the control hole has a circular shape, and the flow of the gas from the second chamber to the first chamber stops when $$P1+\rho gh+\sigma/R=P2,$$

where P1 is the pressure of the first chamber, P2 is the pressure of the second chamber, $\rho$ is a density of the second liquid, g is an acceleration due to gravity, h is a height of the second liquid retained in the support tube, $\sigma$ is a surface tension coefficient of the second liquid, and R is a diameter of the control hole.

4. The suction discharge unit according to claim 1, wherein the negative pressure control unit is in the second chamber.

5. The suction discharge unit according to claim 1, further comprising:
a filter between the storage chamber and the suction source.

6. The suction discharge unit according to claim 1, further comprising:
a pressure adjusting chamber having the second connection hole communicating with the suction source, communicating with the second chamber via a connection pipe and adjusting the pressure of the second chamber.

7. The suction discharge unit according to claim 1, further comprising:
a control member having the control hole;
a liquid passage hole provided in the negative pressure control unit, allowing a liquid retained on a side of the first chamber of the control member to flow into the liquid retaining part, and having a larger opening area than the control hole;
a valve body making the liquid passage hole switchable between a sealed state and an open state; and
an urging member connected to the valve body and urging the valve body in a direction so as to seal the liquid passage hole.

8. The suction discharge unit according to claim 7, wherein the liquid passage hole is positioned at an identical height as the control hole or at a lower height than the control hole in a height direction.

9. The suction discharge unit according to claim 7, further comprising:
a seal releasing member connected to or contacting with the valve body and operable so to release the sealed state of the liquid passage hole realized by the valve body.

10. The suction discharge unit according to claim 9, wherein the urging member has elasticity, and
the seal releasing member releases the sealed state of the control hole realized by the valve body by causing the urging member to elastically deform.

11. The suction discharge unit according to claim 9, wherein the seal releasing member is configured to press the valve body and thereby release the sealed state of the liquid passage hole realized by the valve body.

12. The suction discharge unit according to claim 9, wherein the seal releasing member is configured to separate the valve body from the liquid passage hole and thereby release the sealed state of the liquid passage hole realized by the valve body.

13. A suction discharge device comprising:
the suction discharge unit according to claim 1; and
a suction source connected to the suction discharge unit.

14. The suction discharge unit according to claim 2, wherein the negative pressure control unit is in the second chamber.

15. The suction discharge unit according to claim 3, wherein the negative pressure control unit is in the second chamber.

16. The suction discharge unit according to claim 2, further comprising:
a filter between the storage chamber and the suction source.

17. The suction discharge unit according to claim 3, further comprising:
a filter between the storage chamber and the suction source.

* * * * *